US010993477B2

(12) United States Patent
Yamada et al.

(10) Patent No.: US 10,993,477 B2
(45) Date of Patent: May 4, 2021

(54) FLAVOR INHALER CARTRIDGE AND FLAVOR INHALER

(71) Applicant: JAPAN TOBACCO INC., Tokyo (JP)

(72) Inventors: Manabu Yamada, Tokyo (JP); Takuma Nakano, Tokyo (JP); Kei Oishi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 305 days.

(21) Appl. No.: 16/168,376

(22) Filed: Oct. 23, 2018

(65) Prior Publication Data

US 2019/0053544 A1 Feb. 21, 2019

Related U.S. Application Data

(63) Continuation of application No. PCT/JP2016/063153, filed on Apr. 27, 2016.

(51) Int. Cl.
*A24F 47/00* (2020.01)
*A61M 15/06* (2006.01)
*A61M 15/00* (2006.01)

(52) U.S. Cl.
CPC ............ *A24F 47/008* (2013.01); *A24F 47/00* (2013.01); *A61M 15/06* (2013.01); *A61M 15/0021* (2014.02); *A61M 15/0086* (2013.01)

(58) Field of Classification Search
CPC ....... A24F 40/40; A24F 40/485; A24F 47/008
See application file for complete search history.

(56) References Cited

U.S. PATENT DOCUMENTS

| 2011/0315152 A1 | 12/2011 | Hearn et al. | |
| 2012/0111347 A1* | 5/2012 | Hon | H05B 3/06 131/329 |

(Continued)

FOREIGN PATENT DOCUMENTS

| CN | 204796751 U | 11/2015 |
| CN | 204907926 U | 12/2015 |

(Continued)

OTHER PUBLICATIONS

CN 205040658 Translation; Feb. 24, 2016 (Year: 2016).*

(Continued)

*Primary Examiner* — Eric Yaary
(74) *Attorney, Agent, or Firm* — Birch, Stewart, Kolasch & Birch LLP

(57) ABSTRACT

A flavor inhaler cartridge includes a housing, a movable lid member, an aerosol flow passage, a turning member, and a motion conversion mechanism. The housing includes a reservoir space to house a liquid and an atomizing space to atomize the liquid. With the movable lid member, the reservoir space and the atomizing space are openably/closably partitioned. The aerosol flow passage supplies an aerosol generated by the atomization of the liquid from the atomizing space to outside of the housing. The motion conversion mechanism converts the circumferential turning motion of the turning member into an axial linear motion of the lid member. The lid member is fixed to the motion conversion mechanism. The motion conversion mechanism is configured such that circumferentially turning the turning member moves the lid member in a direction of approaching the turning member and communicates between the reservoir space and the atomizing space.

37 Claims, 10 Drawing Sheets

(56) References Cited

U.S. PATENT DOCUMENTS

| | | | |
|---|---|---|---|
| 2014/0150783 A1* | 6/2014 | Liu | A24F 47/008 128/202.21 |
| 2014/0360514 A1 | 12/2014 | Zhu | |
| 2015/0144147 A1 | 5/2015 | Li et al. | |
| 2015/0282530 A1 | 10/2015 | Johnson et al. | |
| 2016/0227841 A1* | 8/2016 | Li | A61M 15/06 |
| 2016/0249683 A1 | 9/2016 | Li et al. | |
| 2016/0262455 A1* | 9/2016 | Chen | A24F 47/008 |
| 2017/0295847 A1 | 10/2017 | Liu | |
| 2018/0098575 A1* | 4/2018 | Liu | A24F 47/008 |

FOREIGN PATENT DOCUMENTS

| | | |
|---|---|---|
| CN | 205040558 U | 2/2016 |
| EP | 2 823 720 A1 | 1/2015 |
| EP | 2 891 415 A2 | 7/2015 |
| JP | 2012-513275 A | 6/2012 |
| KR | 10-1454125 B1 | 10/2014 |
| WO | WO 2013/118299 A1 | 8/2013 |
| WO | WO 2014/115324 A | 7/2014 |
| WO | WO 2016/049876 A1 | 4/2016 |

OTHER PUBLICATIONS

International Search Report for PCT/JP2016/063153 dated Jun. 21, 2016.
Korean Office Action dated Jun. 18, 2020, for corresponding Korean Application No. 10-2018-7033776, with an English translation.
Chinese Office Action and Search Report for Chinese Application No. 201680084997.0, dated Aug. 28, 2020, with English translation of the Office Action.
Extended European Serach Report, dated Nov. 12, 2019, for European Application No. 16900417.3.

\* cited by examiner

FLAVOR INHALER CARTRIDGE AND FLAVOR INHALER

CROSS REFERENCE TO RELATED APPLICATIONS

The present application is a continuation application of International Application No. PCT/JP2016/063153, filed on Apr. 27, 2016. The contents of these applications are incorporated herein by reference in their entirety.

TECHNICAL FIELD

The present invention relates to a flavor inhaler cartridge and a flavor inhaler.

BACKGROUND ART

There has been conventionally known a flavor inhaler to inhale a flavor without burning a material. For example, an electronic cigarette has been known as such flavor inhaler. The electronic cigarette supplies an aerosol generated by atomizing liquid (aerosol source) containing a flavor to a mouth of a user or causes an aerosol generated by atomizing liquid not containing a flavor to pass through a flavor source (for example, a tobacco source) and supplies the mouth of the user with the aerosol.

Some electronic cigarettes include a tank to house the liquid to generate the aerosol and an atomization unit that atomizes this liquid. Some of the above-described electronic cigarettes including the tank include a lid with which the tank and the atomization unit are partitioned to supply the liquid in the tank to the atomization unit. This lid is openably/closably configured, and, for example, the user opens the lid while the electronic cigarette is in use and closes the lid while the electronic cigarette is not in use.

As an open/close mechanism of the lid, for example, there has been known a mechanism that turns a mouthpiece to press down a pipe through which an aerosol passes and open a lid (see PTL 1 and PTL 2). There has been also known an electronic cigarette that engages a battery assembly with an atomizer assembly to open a valve with which a reservoir that houses liquid and an atomizer are partitioned (see PTL 3 and PTL 4).

CITATION LIST

Patent Literature

PTL 1: U.S. Unexamined Patent Application Publication No. 2015/0144147
PTL 2: U.S. Unexamined Patent Application Publication No. 2014/0360514
PTL 3: EP 2891415 A
PTL 4: EP 2823720 A

SUMMARY OF INVENTION

Technical Problem

An object of the present invention is to provide a novel open/close mechanism of a lid with which a reservoir space and an atomizing space are partitioned.

Solution to Problem

According to one aspect of the present invention, there is provided a flavor inhaler cartridge. This flavor inhaler cartridge includes a housing, a movable lid member, an aerosol flow passage, a turning member, and a motion conversion mechanism. The housing includes a reservoir space to house a liquid and an atomizing space to atomize the liquid. With the movable lid member, the reservoir space and the atomizing space are openably/closably partitioned. The aerosol flow passage supplies an aerosol generated by the atomization of the liquid from the atomizing space to outside of the housing. The turning member is circumferentially turnable around an axis parallel to a moving direction of the lid member. The motion conversion mechanism converts the circumferential turning motion of the turning member into an axial linear motion of the lid member. The lid member is directly or indirectly fixed to the motion conversion mechanism. The motion conversion mechanism is configured such that circumferentially turning the turning member moves the lid member in a direction of approaching the turning member and communicates between the reservoir space and the atomizing space.

According to one aspect of the present invention, the atomizing space internally includes an atomizing element to atomize the liquid.

According to one aspect of the present invention, the flavor inhaler cartridge includes a moving member that axially moves together with the lid member. The lid member is indirectly fixed to the motion conversion mechanism via the moving member. The motion conversion mechanism is configured such that the circumferential turning motion of the turning member is converted into axial linear motions of the lid member and the moving member.

According to one aspect of the present invention, the motion conversion mechanism includes an engaged portion disposed on an outer peripheral surface or an inner peripheral surface of the moving member and an engaging portion engaged with the engaged portion. Any one of the engaging portion and the engaged portion has a spiral protrusion with a spiral surface. The other of the engaging portion and the engaged portion have a sliding portion sliding on the spiral surface.

According to one aspect of the present invention, the spiral protrusion and the sliding portion are thread ridges.

According to one aspect of the present invention, the flavor inhaler cartridge includes a reduction member that reduces a leakage of the liquid in the reservoir space from an opening of the housing to the outside of the housing. The opening constitutes a supply port to supply the liquid to the reservoir space.

According to one aspect of the present invention, the reduction member is at least partially made of a flexible material.

According to one aspect of the present invention, the flavor inhaler cartridge includes a partition member that has a communication hole. The communication hole communicates between the reservoir space and the atomizing space. The lid member opens and closes the communication hole such that the reservoir space and the atomizing space are openably/closably partitioned.

According to one aspect of the present invention, the flavor inhaler cartridge includes a moving member that axially moves together with the lid member. The lid member is indirectly fixed to the motion conversion mechanism via the moving member. The motion conversion mechanism is configured such that the circumferential turning motion of the turning member is converted into the axial linear motions of the lid member and the moving member. The moving member is a flow passage pipe constituting at least a part of the aerosol flow passage.

According to one aspect of the present invention, the turning member is configured to be circumferentially turnable around a center axis of the flow passage pipe.

According to one aspect of the present invention, the flavor inhaler cartridge includes a stopper configured to restrict the movement of the lid member. When the lid member moves in the direction of approaching the turning member by a predetermined distance, the stopper contacts the lid member.

According to one aspect of the present invention, the stopper is located in the reservoir space.

According to one aspect of the present invention, the flavor inhaler cartridge includes a moving member that axially moves together with the lid member. The lid member is indirectly fixed to the motion conversion mechanism via the moving member. The motion conversion mechanism is configured such that the circumferential turning motion of the turning member is converted into the axial linear motions of the lid member and the moving member. The flavor inhaler cartridge further includes a stopper configured to restrict the movement of the moving member. When the moving member moves in the direction of approaching the turning member by a predetermined distance, the stopper directly or indirectly contacts the moving member.

According to one aspect of the present invention, the flavor inhaler cartridge includes a biasing member configured to bias the lid member to the atomizing space side.

According to one aspect of the present invention, the flavor inhaler cartridge includes a flow passage pipe that constitutes at least a part of the aerosol flow passage and a reinforcing member that reinforces the flow passage pipe. The biasing member directly or indirectly abuts on the reinforcing member.

According to one aspect of the present invention, the turning member is a mouthpiece. The mouthpiece constitutes at least a part of the aerosol flow passage. The mouthpiece is disposed downstream with respect to the reservoir space in the aerosol flow passage.

According to one aspect of the present invention, the mouthpiece includes a flow pipe through which the aerosol flows and a restricting member configured to contact the housing to restrict an axial movement of the mouthpiece toward the lid member.

According to one aspect of the present invention, the flow pipe is held to the restricting member to be circumferentially turnable. The motion conversion mechanism is configured to convert the circumferential turning motion of the flow pipe into the axial linear motion of the lid member.

According to one aspect of the present invention, the turning member is located downstream with respect to the lid member in the aerosol flow passage.

According to one aspect of the present invention, the flavor inhaler cartridge includes a partition member having a communication hole that communicates between the reservoir space and the atomizing space. The lid member opens and closes the communication hole such that the reservoir space and the atomizing space are openably/closably partitioned. The partition member includes a plate-shaped portion that has an opening through which the aerosol generated in the atomizing space passes. The opening constitutes at least a part of the aerosol flow passage. The communication hole is formed in the plate-shaped portion.

According to one aspect of the present invention, the partition member includes a tubular portion. The tubular portion is joined to the plate-shaped portion. The tubular portion internally communicates with the opening in the plate-shaped portion.

According to one aspect of the present invention, the lid member includes a lid portion. The lid portion abuts on the plate-shaped portion along a whole circumference of the plate-shaped portion to close the communication hole.

According to one aspect of the present invention, the lid member includes a lid portion. The lid portion partially abuts on the plate-shaped portion along a peripheral area of the plate-shaped portion to close the communication hole.

According to one aspect of the present invention, the lid member is located in the reservoir space.

According to one aspect of the present invention, the flavor inhaler cartridge includes an atomizing element located in the atomizing space to atomize the liquid and a partition member that has the communication hole that communicates between the reservoir space and the atomizing space. The lid member opens and closes the communication hole such that the reservoir space and the atomizing space are openably/closably partitioned. The atomizing element includes a heating wire. The heating wire is formed into a spiral shape around an axis approximately parallel to an axis of the housing in a longitudinal direction.

According to one aspect of the present invention, the flavor inhaler cartridge includes a first liquid holding member that holds the liquid supplied via the communication hole. The first liquid holding member is located in the atomizing space.

According to one aspect of the present invention, the first liquid holding member is formed into an approximately tubular shape and has an internal space. At least a part of the heating wire is located in the internal space in the first liquid holding member.

According to one aspect of the present invention, the heating wire of the atomizing element is formed into a spiral shape around a center axis of the approximately tubular first liquid holding member.

According to one aspect of the present invention, the heating wire of the atomizing element contacts an inner wall of the first liquid holding member.

According to one aspect of the present invention, the first liquid holding member is located in the atomizing space so as to cover the communication hole.

According to one aspect of the present invention, the flavor inhaler cartridge includes an atomizing element located in the atomizing space to atomize the liquid and a partition member having a communication hole that communicates between the reservoir space and the atomizing space. The lid member opens and closes the communication hole such that the reservoir space and the atomizing space are openably/closably partitioned. The atomizing element includes a heating wire. The heating wire is formed into a spiral shape around an axis approximately perpendicular to an axis of the housing in a longitudinal direction.

According to one aspect of the present invention, the flavor inhaler cartridge includes a flat-plate-shaped first liquid holding member that holds the liquid supplied via the communication hole. The first liquid holding member is located in the atomizing space.

According to one aspect of the present invention, the first liquid holding member is located in the atomizing space so as to cover the communication hole.

According to one aspect of the present invention, the flavor inhaler cartridge includes a second liquid holding member that holds the liquid supplied via the communication hole. The heating wire is wound around the second liquid holding member.

According to one aspect of the present invention, the flavor inhaler cartridge includes the flat-plate-shaped first liquid holding member that holds the liquid supplied via the communication hole. The first liquid holding member is located in the atomizing space. The second liquid holding member contacts the first liquid holding member.

One aspect of the present invention provides a flavor inhaler. The flavor inhaler includes any one of the above-described flavor inhaler cartridges.

According to one aspect of the present invention, the flavor inhaler includes the atomizing element located in the atomizing space to atomize the liquid and an electric power supply unit that supplies the atomizing element with electric power.

According to one aspect of the present invention, the electric power supply unit includes the turning member.

DESCRIPTION OF EMBODIMENTS

Figure 1:
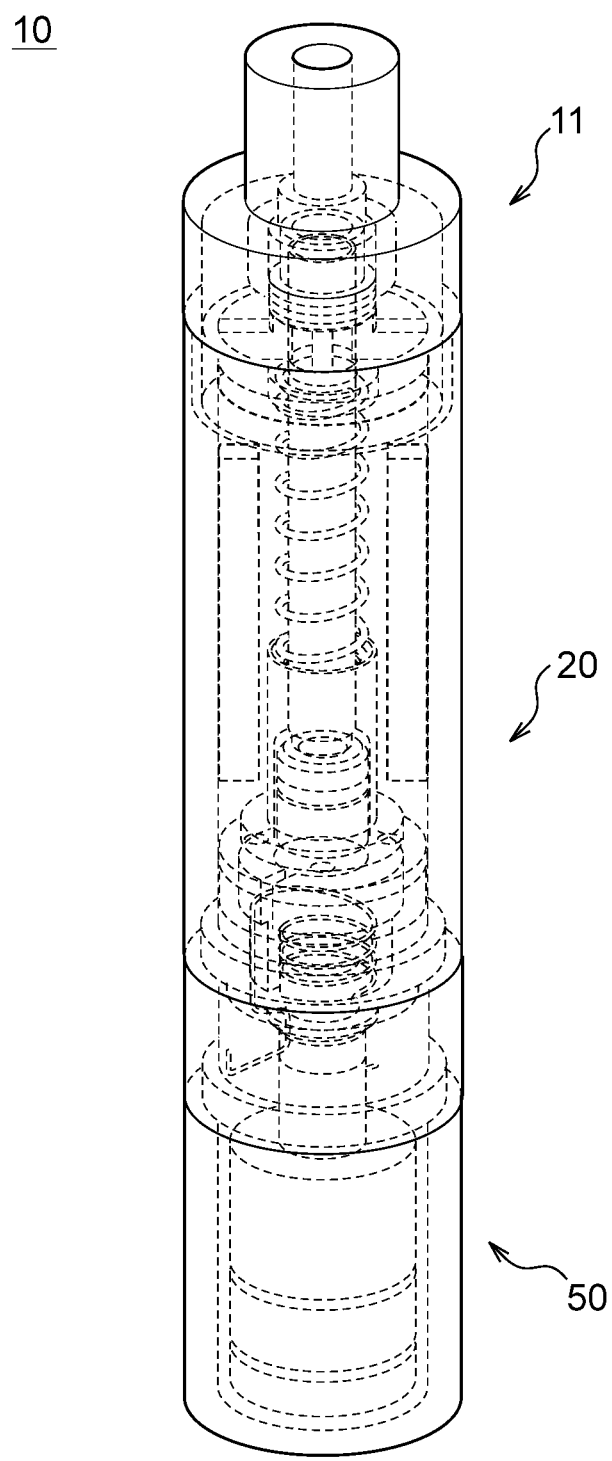
FIG. 1 is an overall perspective view of a flavor inhaler according to an embodiment.

The following describes an embodiment of the present invention with reference to the drawings. In the drawings described later, the identical reference numerals are assigned for the identical or equivalent elements, and therefore such elements will not be further elaborated here.

Figure 2:
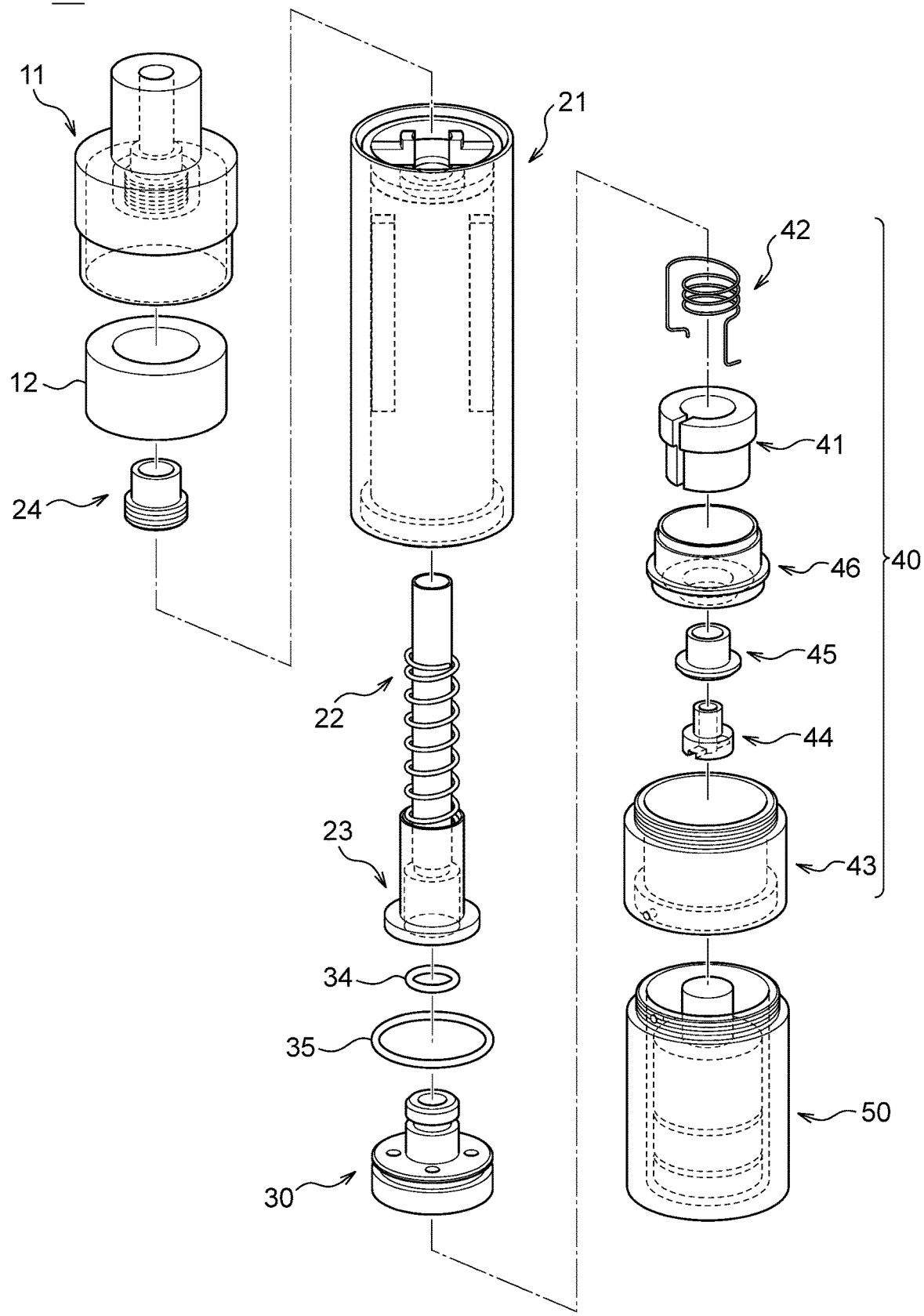
FIG. 2 is an exploded perspective view of the flavor inhaler according to the embodiment.

FIG. 1 is an overall perspective view of a flavor inhaler according to the embodiment. FIG. 2 is an exploded perspective view of the flavor inhaler according to the embodiment. As illustrated in FIG. 1, a flavor inhaler 10 includes a mouthpiece 11, an atomizer unit 20, and a battery unit 50 (equivalent to one example of an electric power supply unit). The atomizer unit 20 atomizes, for example, liquid containing a flavor containing a component such as nicotine and supplies an aerosol. The battery unit 50 supplies the atomizer unit 20 with electric power. The mouthpiece 11 guides the aerosol generated at the atomizer unit 20 to a mouth of a user. The mouthpiece 11 and the atomizer unit 20 are replaceable after the flavor inhaler 10 is used for a predetermined period. That is, in this embodiment, a part excluding the battery unit 50 from the flavor inhaler 10 serves as a flavor inhaler cartridge.

As illustrated in FIG. 2, the mouthpiece 11 includes a silicon ring 12. The atomizer unit 20 includes a screw portion 24, a housing 21, a flow passage pipe 22 (equivalent to one example of a moving member), a lid member 23, a first O-ring 34, a second O-ring 35, a partition member 30, and an atomizing unit 40 (equivalent to one example of an atomizing element). The atomizing unit 40 includes a first liquid holding member 41, a heating wire 42, an outer housing 43, an electrode 44, an insulating ring 45, and a supporter 46.

Figure 3:
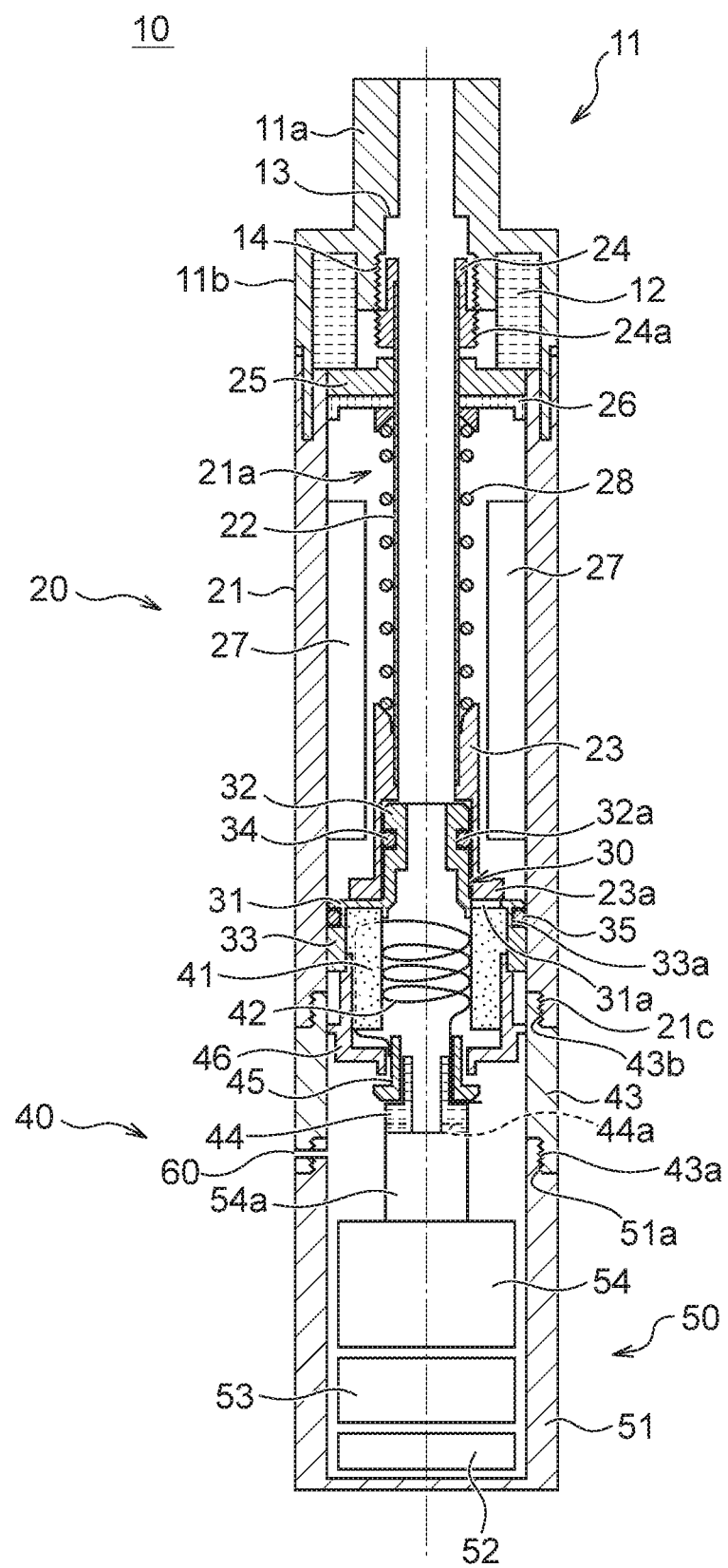
FIG. 3 is a cross-sectional view of the flavor inhaler in a state where a reservoir space and an atomizing space are partitioned.

FIG. 3 is a cross-sectional view of the flavor inhaler in a state where a reservoir space and an atomizing space are partitioned. In this embodiment, a space upstream with respect to the partition member 30 and where the aerosol is generated is referred to as an atomizing space and a space downstream with respect to the partition member 30 and where liquid in the housing 21 is housed is referred to as the reservoir space. The upstream and the downstream in this description mean an upstream side and a downstream side of an air flow passage in the flavor inhaler 10. In this embodiment, the downstream side is equivalent to an inhale port side where the mouthpiece 11 is located and the upstream side means the opposite side. The flavor inhaler of this embodiment can house liquid in the reservoir space. This liquid (aerosol source) may be liquid containing a flavor source such as nicotine or may be liquid not containing the flavor source such as the nicotine.

As illustrated in FIG. 3, the battery unit 50 includes a battery housing 51, a light source 52 such as a light-emitting diode, a control unit 53, and a battery 54. The battery housing 51 houses the light source 52, the control unit 53, and the battery 54. A screw 51a engaged with the outer housing 43, which is provided with the atomizer unit 20, is formed on an outer peripheral surface at an end in the downstream side of the battery housing 51.

The control unit 53 includes, for example, an electronic circuit board and an airflow sensor. The electronic circuit board controls an electronic circuit such that the battery 54 supplies the electric power not only to the heating wire 42 of the atomizing unit 40 but also to the light source 52. The airflow sensor senses an air pressure change or an airflow generated in the flavor inhaler 10 when the user inhales the air from the mouthpiece 11. When the airflow sensor senses the air pressure change or the airflow, the electronic circuit board causes the battery 54 to supply the heating wire 42 and the light source 52 with the electric power.

The battery 54 is connected to a positive electrode terminal 54a connected to the electrode 44 of the atomizing unit 40. By coupling the battery housing 51 to the outer housing 43 of the atomizing unit 40, the battery 54 contacts and is electrically connected to the electrode 44 via the positive electrode terminal 54a. The battery 54 is connected to a negative electrode terminal (not illustrated). By coupling the battery housing 51 to the outer housing 43 of the atomizing unit 40, the negative electrode terminal is configured to be electrically connected to the supporter 46.

The first liquid holding member 41 of the atomizing unit 40, which is made of a material such as cotton, glass fiber, and porous ceramic, is configured to hold the liquid generating the aerosol. Specifically, the first liquid holding member 41 is located in the atomizing space so as to cover communication holes 31a, which will be described later, on the partition member 30 to hold the liquid supplied from the reservoir space via the communication holes 31a. Since the first liquid holding member 41 contacts the heating wire 42 as described later, the first liquid holding member 41 is preferably made of glass fiber or porous ceramic, which is a material excellent in heat resistance. The first liquid holding member 41 is formed into an approximately tubular shape and has an internal space. At least a part of the heating wire 42 is located in this internal space. The first liquid holding member 41 may have a multilayer structure formed by stacking approximately tubular-shaped members having different diameters. Specifically, for example, the part constituting the above-described internal space in which the heating wire 42 is located is configured as a first-layer liquid holding member and a second-layer liquid holding member may be located so as to be in contact with the outer peripheral side. In such case, the respective members can be made of different materials.

The heating wire 42 is formed into a spiral shape around an axis approximately parallel to an axis of the housing 21 in the longitudinal direction. The heating wire 42 is configured to heat and atomize the liquid held in the first liquid holding member 41 to generate the aerosol. The heating wire 42 is configured to be in contact with an inner wall (inner peripheral surface) of the first liquid holding member 41. In one embodiment, the heating wire 42 can be formed into a spiral shape around the center axis of the tubular first liquid holding member 41. The heating wire 42 includes a lead wire on a positive electrode side and a lead wire on a negative electrode side. Specifically, the lead wire on the positive electrode side of the heating wire 42 is maintained in a state of being sandwiched between the electrode 44 and the insulating ring 45 and contacting the electrode 44. Meanwhile, the lead wire on the negative electrode side of the heating wire 42 passes through the outside of the first liquid holding member 41 and is sandwiched between the supporter 46 and the insulating ring 45. The respective lead wire on the positive electrode side and lead wire on the negative electrode side of the heating wire 42 may be connected to the electrode 44 and the supporter 46 by welding, soldering, or similar method.

The outer housing 43 includes a screw 43a engaging with the screw 51a of the battery housing 51 on an inner peripheral surface at the end in the upstream side. At the part where the outer housing 43 and the battery housing 51 are engaged with the screws, an air hole 60 communicating between the outside and the inside of the flavor inhaler 10 is disposed. Note that the air hole 60 can be disposed at any position on the battery housing 51 and on the battery unit 50 side with respect to the supporter 46 in the outer housing 43.

The supporter 46 is electrically connected to the lead wire on the negative electrode side of the heating wire 42 and the negative electrode terminal (not illustrated) connected to the battery 54. The supporter 46 is a conductive member, fixed to the inside of the outer housing 43, and supports the heating wire 42, the electrode 44, and the insulating ring 45. The supporter 46 is electrically connected to the negative electrode terminal connected to the battery 54 and connected to the lead wire on the negative electrode side of the heating wire 42, thereby serving as a negative electrode that supplies the electric power from the battery unit 50 to the heating wire 42. The lead wire on the negative electrode side of the heating wire 42 may be configured to directly contact the negative electrode terminal (not illustrated) connected to the battery 54. In this case, the supporter 46 can be formed from an insulating member. In this embodiment, a relationship between the positive and the negative of the electrode may be the opposite. The insulating ring 45 is disposed such that the lead wire on the negative electrode side of the heating wire 42 is electrically connected to the supporter 46 and the lead wire on the positive electrode side of the heating wire 42 is electrically connected to the electrode 44. The outer housing 43 includes a screw 43b that engages with a screw 21c of the housing 21 on the outer peripheral surface at the end on the downstream side.

The partition member 30 includes a plate-shaped portion 31, a tubular portion 32, which is joined to the surface on the downstream side of the plate-shaped portion 31, and a tubular extending portion 33, which extends to the upstream side of the plate-shaped portion 31, and defines a boundary between the reservoir space and the atomizing space. The plate-shaped portion 31 has the plurality of communication holes 31a to communicate between the reservoir space and the atomizing space. The plate-shaped portion 31 has an opening through which the aerosol generated in the atomizing space passes and that constitutes at least a part of an aerosol flow passage at the center. The tubular portion 32 internally communicates with the opening in the plate-shaped portion 31, constitutes at least a part of the aerosol flow passage, and has a groove 32a to which the first O-ring 34 fits on the outer peripheral surface. The first O-ring 34 seals between the partition member 30 and the lid member 23. The extending portion 33 extends from the outer peripheral portion of the plate-shaped portion 31 to the upstream side and has a groove 33a to which the second O-ring 35 fits on the outer peripheral surface. The second O-ring 35 seals between the partition member 30 and the housing 21.

The flow passage pipe 22 is housed in the housing 21 and configured to be axially movable. The flow passage pipe 22 constitutes at least a part of the aerosol flow passage and supplies the aerosol generated in the atomizing space to the mouthpiece 11. The lid member 23 with which the reservoir space and the atomizing space are openably/closably partitioned is fixed to the upstream side of the flow passage pipe 22. The lid member 23 is configured to be axially movable together with the flow passage pipe 22 and is located in the reservoir space downstream with respect to the partition member 30. The lid member 23 contacts the plate-shaped portion 31 of the partition member 30 and opens and closes the communication holes 31a on the partition member 30. The cylindrical screw portion 24, which includes a thread ridge 24a (equivalent to one example of an engaged portion) on the outer peripheral surface, is fixed to the downstream side of the flow passage pipe 22.

The lid member 23 is entirely formed into an approximately tubular shape and mounted to an outer peripheral surface of the flow passage pipe 22. The lid member 23 includes a disk-shaped lid portion 23a that abuts on the plate-shaped portion 31 of the partition member 30 along the whole circumference to close the communication holes 31a. The aerosol generated by the heating wire 42 passes through the inside of the lid member 23, which constitutes a part of the aerosol flow passage.

A spiral spring 28 (equivalent to one example of a biasing member) is disposed at the outer periphery of the flow passage pipe 22. One end of the spring 28 is supported to the lid member 23 so as to bias the lid member 23 to the atomizing space side. Accordingly, the spring 28 usually biases the lid member 23 such that the lid member 23 closes the communication holes 31a on the partition member 30.

The other end of the spring 28 abuts on the surface in the upstream side of a reduction member 26.

The housing 21 includes a pair of axially extending ribs 27 on the inner surface. In other words, the ribs 27 are located in the reservoir space. The downstream movement of the lid member 23 causes the ribs 27 to abut on the lid member 23, and thus the ribs 27 serve as stoppers to restrict the movement of the lid member 23. The housing 21 includes a pair of radially extending reinforcing members 25 at the inner surface downstream with respect to the ribs 27. The reinforcing members 25 abut on the outer peripheral surface of the flow passage pipe 22 to reinforce the flow passage pipe 22 so as to reduce a position shift and a deformation of the flow passage pipe 22. Between the reinforcing members 25 and the spring 28, the reduction member 26 that reduces a leakage of the liquid in the reservoir space from the opening 21a of the housing 21 to the outside of the housing 21 is located.

Figure 6:
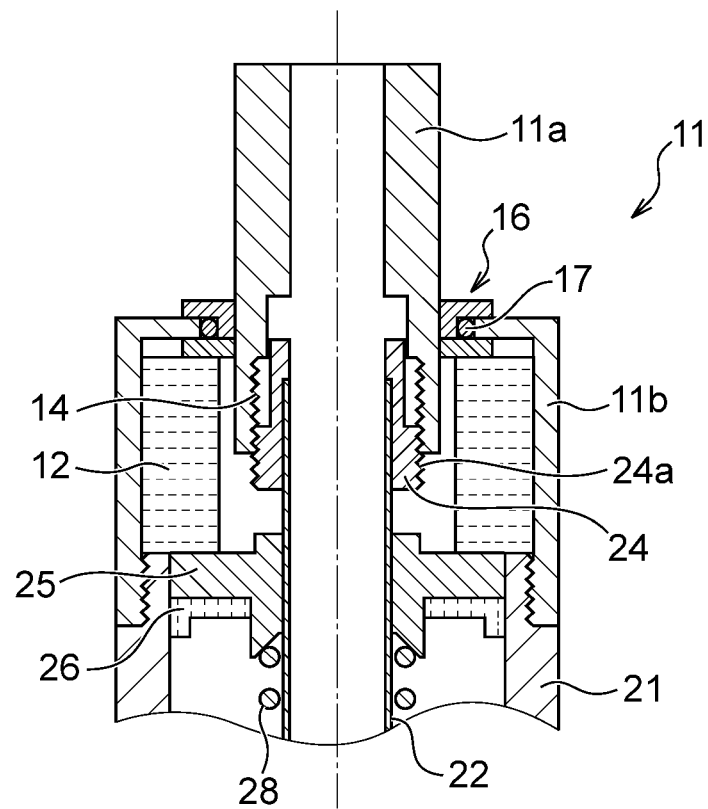
FIG. 6 is a cross-sectional view illustrating another configuration of a mouthpiece provided with the flavor inhaler.

The reduction member 26 is sandwiched between the spring 28 and the reinforcing members 25 to be fixed at the inside of the housing 21. The reduction member 26 has a hole through which the flow passage pipe 22 passes and is at least partially made of a flexible material such as silicon. When the reservoir space is filled or supplemented with liquid, while the part made of the flexible material in the reduction member 26 is pushed and bent with, for example, tops of a dropper and a syringe, this top is located in the reservoir space, thus ensuring supplying the liquid. That is, the opening of the housing 21 constitutes a supply port to supply the liquid to the reservoir space. The spring 28 is supported by the reinforcing members 25 fixed to the housing 21 via the reduction member 26. Accordingly, the spring 28 indirectly abuts on the reinforcing members 25 in this embodiment. As illustrated in FIG. 6 described later, the spring 28 may be configured to directly abut on the reinforcing members 25. In one embodiment, the reduction member 26 may be located at the downstream side of the reinforcing members 25.

The mouthpiece 11 includes a flow pipe 11a through which the aerosol generated at the atomizer unit 20 flows and a tubular body 11b (equivalent to one example of a restricting member) joined to the flow pipe 11a. The silicon ring 12 is located in the tubular body 11b. The silicon ring 12 reduces a leakage of the liquid in the reservoir space.

On the inner peripheral surface in the upstream side of the flow pipe 11a, a thread ridge 14 (equivalent to one example of an engaging portion) engageable with the thread ridge 24a of the screw portion 24 fixed to the flow passage pipe 22 is formed. The thread ridge 14 of the flow pipe 11a and the thread ridge 24a of the screw portion 24 have typical thread ridge shapes, which have spiral protrusion shapes with spiral surfaces. The thread ridge 14 and the thread ridge 24a constitute sliding portions that slide on the mutual spiral surfaces. Accordingly, the thread ridge 14 and the thread ridge 24a are threadably engageable with one another. As illustrated in FIG. 3, the thread ridge 14 of the mouthpiece 11 contacts the thread ridge 24a of the screw portion 24 with the tubular body 11b abutting on the housing 21. In this state, circumferentially turning the mouthpiece 11 causes the thread ridge 14 of the mouthpiece 11 to threadably engage with the thread ridge 24a of the screw portion 24. At this time, since the tubular body 11b of the mouthpiece 11 contacts the housing 21, the axial movement of the mouthpiece 11 is restricted. Accordingly, by the engagement of the thread ridge 14 of the mouthpiece 11 with the thread ridge 24a of the screw portion 24, the screw portion 24, the flow passage pipe 22, and the lid member 23 move in a direction of approaching the mouthpiece 11. That is, the thread ridge 14 of the mouthpiece 11 and the thread ridge 24a of the screw portion 24 constitute a motion conversion mechanism that converts the circumferential turning motion of the mouthpiece 11 around the axis parallel to the moving direction of the lid member 23 into an axial linear motion of the lid member 23. Note that, in this embodiment, the center axis of the flow pipe 11a of the mouthpiece 11 matches the center axis of the flow passage pipe 22. In view of this, the mouthpiece 11 is configured to be circumferentially turnable around the center axis of the flow passage pipe 22.

Figure 4:
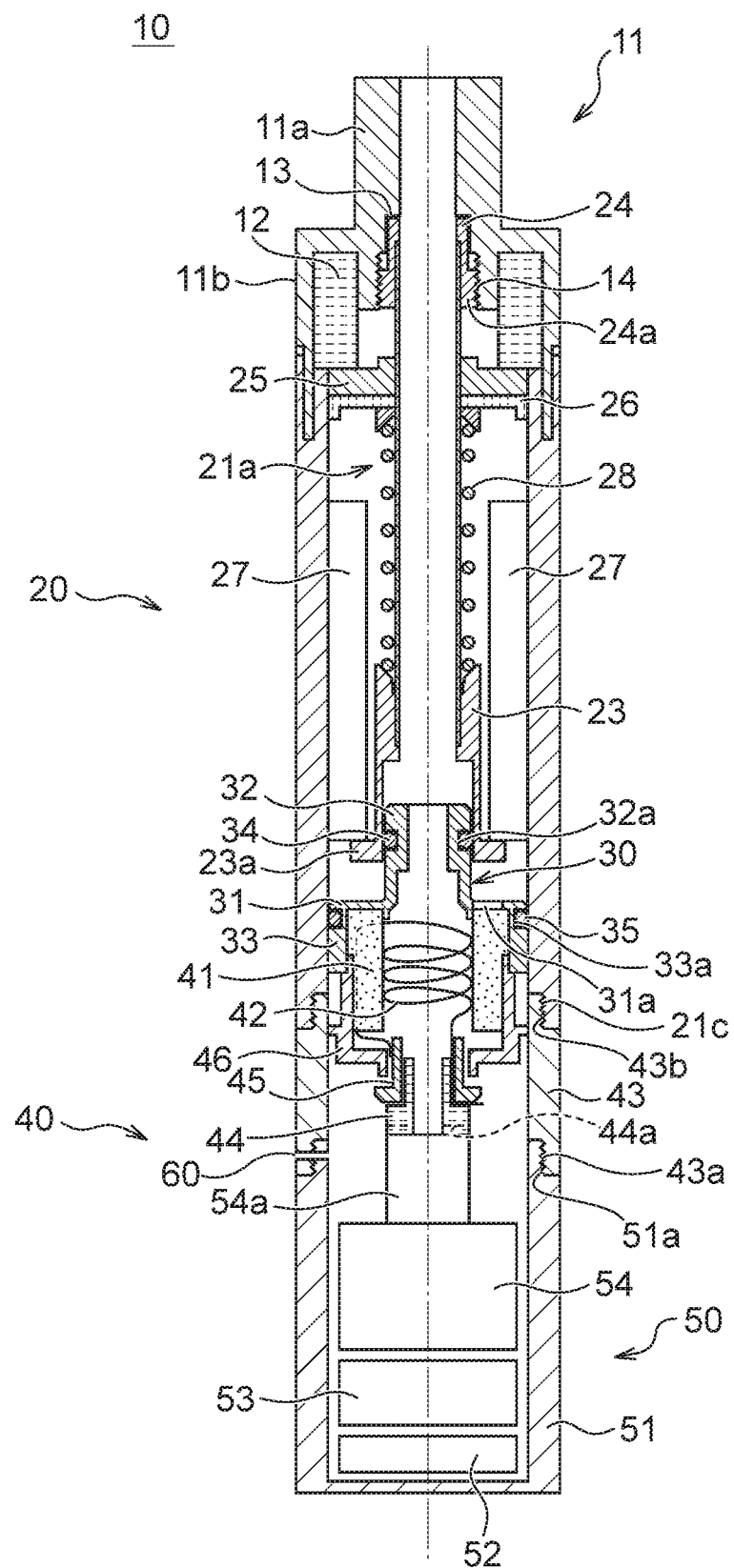
FIG. 4 is a cross-sectional view of the flavor inhaler in a state where the reservoir space communicates with the atomizing space.

FIG. 4 is a cross-sectional view of the flavor inhaler in a state where the reservoir space communicates with the atomizing space. As illustrated in FIG. 4, the threadable engagement of the thread ridge 14 of the mouthpiece 11 with the thread ridge 24a of the screw portion 24 moves the screw portion 24, the flow passage pipe 22, and the lid member 23 in the direction of approaching the mouthpiece 11 and the communication holes 31a on the partition member 30 are opened with the lid member 23. This communicates between the reservoir space and the atomizing space. The lid member 23 that has moved in the direction of approaching the mouthpiece 11 by a predetermined distance contacts the ribs 27, thus restricting the additional movement. Similarly, a stepped portion 13 is formed on the inner peripheral surface of the flow pipe 11a of the mouthpiece 11, and the screw portion 24 fixed to the flow passage pipe 22 that has moved in the direction of approaching the mouthpiece 11 by the predetermined distance contacts this stepped portion 13, thus restricting the additional movement. While the flavor inhaler 10 of this embodiment includes the ribs 27 and the stepped portion 13, the flavor inhaler 10 may include only any one of them.

As illustrated in FIG. 4, when the reservoir space communicates with the atomizing space, the liquid in the reservoir space moves to the first liquid holding member 41 and the first liquid holding member 41 holds the liquid. When the user inhales air from the mouthpiece 11, the airflow sensor in the control unit 53 senses the air pressure change or the airflow caused by the air flown from an air hole (not illustrated) and the electronic circuit board in the control unit 53 causes the battery 54 to supply the heating wire 42 and the light source 52 with the electric power. The supply of the electric power to the heating wire 42 heats the heating wire 42, atomizes the liquid held in the first liquid holding member 41, and generates the aerosol. When the user inhales air from the mouthpiece 11, the air is flown from the air hole 60 into the flavor inhaler 10, passes through the air flow passage including a groove 44a disposed on the electrode 44, the atomizing space, the tubular portion 32 of the partition member 30, the lid member 23, the flow passage pipe 22, and the flow pipe 11a, and then is guided into the mouth of the user. Accordingly, the aerosol generated in the atomizing space passes through the aerosol flow passage, which is configured of the tubular portion 32 of the partition member 30, the lid member 23, the flow passage pipe 22, and the flow pipe 11a, together with the air flown from the air hole 60, and then is guided into the mouth of the user.

In the state illustrated in FIG. 4, turning the mouthpiece 11 in the reverse direction releases the threadable engagement of the thread ridge 14 of the mouthpiece 11 with the thread ridge 24a of the screw portion 24 and moves the lid member 23 to the atomizing space side. The lid member 23 is biased toward the partition member 30 by the spring 28. This closes the communication holes 31a on the partition member 30 by the lid member 23 and the state returns to the state illustrated in FIG. 3.

As described above, with the flavor inhaler 10 illustrated in FIG. 1 to FIG. 4, turning the mouthpiece 11 moves the lid member 23 in the direction of approaching the mouthpiece 11 to ensure the communication between the reservoir space and the atomizing space. Additionally, with this flavor inhaler 10, since the lid member 23 can be located in the reservoir space, the atomizing space can be configured to be smaller than the case of disposing the lid member 23 in the atomizing space.

While this embodiment includes the thread ridge 14 of the mouthpiece 11, the configuration is not limited to this. The thread ridge 14 can be disposed on any member that circumferentially turns around the axis parallel to the moving direction of the lid member 23. In this embodiment, the lid member 23 is connected to the screw portion 24 via the flow passage pipe 22. However, the configuration is not limited to this. The lid member 23 may be connected to the screw portion 24 directly or via any member configured to be axially movable. The flavor inhaler 10 illustrated from FIG. 1 to FIG. 4 includes the thread ridge 14 on the inner peripheral surface of the flow pipe 11a and includes the thread ridge 24a on the outer peripheral surface of the screw portion 24. In the opposite way, the thread ridge 14 may be formed on the outer peripheral surface of the flow pipe 11a and the thread ridge 24a may be formed on the inner peripheral surface of the screw portion 24. In the flavor inhaler 10 illustrated from FIG. 1 to FIG. 4, while the housing 21 also serves as the tank for liquid, instead of this, a housing for a liquid tank may be disposed in the housing 21.

This embodiment describes that the part excluding the battery unit 50 from the flavor inhaler 10 is the replaceable cartridge of the flavor inhaler 10. However, the configuration is not limited to this, and the cartridge of the flavor inhaler 10 only needs to include at least a reservoir space (liquid tank) part to house the liquid. That is, the flavor inhaler 10 of this embodiment only needs to be configured such that at least the reservoir space (liquid tank) part is replaceable. While the flavor inhaler 10 of this embodiment is described that the cartridge part is replaceable, the configuration is not limited to this, and the flavor inhaler 10 can be configured so as not to allow a partial replace. In this case, the user can repeatedly use the flavor inhaler 10 by appropriately supplementing the liquid in the reservoir space.

Figure 5:
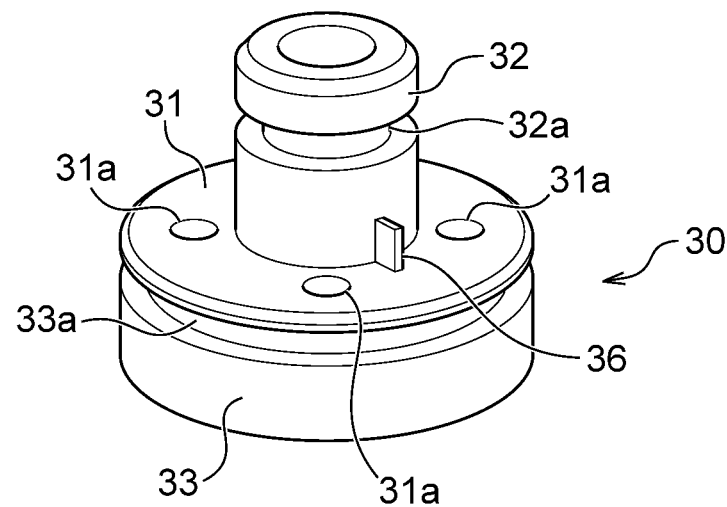
FIG. 5 is a perspective view illustrating another configuration of a partition member provided with the flavor inhaler.

Next, the following describes another configuration example that can be provided with the flavor inhaler 10. FIG. 5 is a perspective view illustrating another configuration of the partition member 30 provided with the flavor inhaler 10. As illustrated in FIG. 5, the partition member 30 includes a rib 36 extending upward from the plate-shaped portion 31. The rib 36 is also fixed to the outer peripheral surface of the tubular portion 32. When the flavor inhaler 10 includes the partition member 30 illustrated in FIG. 5, the lid member 23 illustrated from FIG. 1 to FIG. 4 is configured so as to include a groove corresponding to the rib 36. Circumferentially rotating the mouthpiece 11 to threadably engage the thread ridge 14 with the thread ridge 24a of the screw portion 24, a circumferential force (a friction force) caused by the threadable engagement is applied to the screw portion 24. In view of this, the screw portion 24, the flow passage pipe 22, and the lid member 23 possibly circumferentially rotate. By the partition member 30 including the rib 36, when the lid member 23 contacts the partition member 30 so as to close the communication holes 31a, the rib 36 is inserted into the groove disposed on the lid member 23. This allows reliably preventing the circumferential rotation of the lid member 23, the flow passage pipe 22, and the screw portion 24.

FIG. 6 is a cross-sectional view illustrating another configuration of the mouthpiece 11 provided with the flavor inhaler 10. As illustrated in FIG. 6, this mouthpiece 11 includes the flow pipe 11a and the tubular body 11b separately. The tubular body 11b is fixed to the housing 21 by threadable engagement. A seal holding member 16 that includes a ring having an approximately L-shape in the cross-sectional surface and a rectangular cross-sectional ring is fixed to the outer peripheral surface of the flow pipe 11a. An O-ring 17 is located between the seal holding member 16 and the tubular body 11b to reduce a leakage of external air from between the flow pipe 11a and the tubular body 11b. Accordingly, the flow pipe 11a is held by the tubular body 11b to be circumferentially turnable.

To threadably engage the thread ridge 14 of the flow pipe 11a with the thread ridge 24a of the screw portion 24, the flow pipe 11a of the mouthpiece 11 is circumferentially turned. At this time, the tubular body 11b is fixed to the housing 21 and does not turn, and the flow pipe 11a and the seal holding member 16 turn. With the flavor inhaler 10 illustrated in FIG. 6, the lid member 23 can be opened and closed with the mouthpiece 11 mounted to the housing 21. In the example of the flavor inhaler 10 illustrated in FIG. 6, a part of the reinforcing members 25 penetrate the reduction member 26 and extend to the upstream side. In this example, the spring 28 directly abuts on the reinforcing members 25.

Figure 7A:
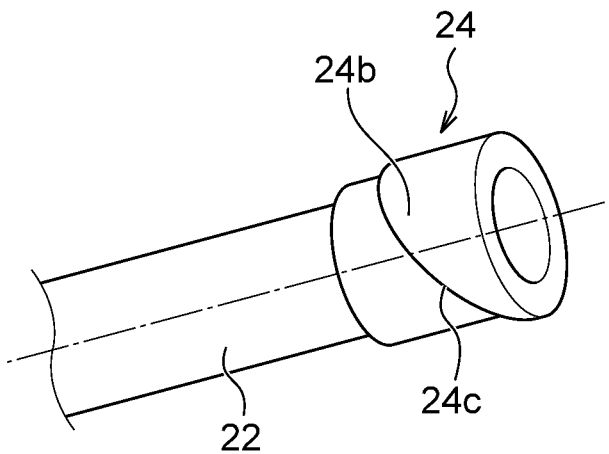
FIG. 7A is a perspective view illustrating another configuration of a flow passage pipe provided with the flavor inhaler.
Figure 7B:
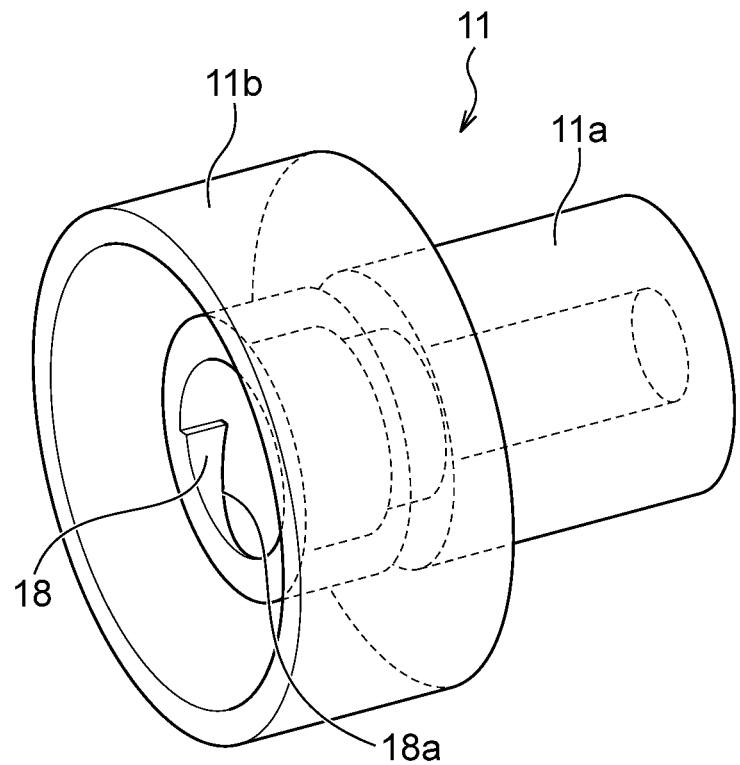
FIG. 7B is a perspective view illustrating another configuration of the mouthpiece provided with the flavor inhaler.

FIG. 7A is a perspective view illustrating another configuration of the flow passage pipe 22 provided with the flavor inhaler 10. FIG. 7B is a perspective view illustrating another configuration of the mouthpiece 11 provided with the flavor inhaler 10. As illustrated in FIG. 7A, the screw portion 24 disposed in the upstream side of the flow passage pipe 22 includes a spiral protrusion portion 24b with a spiral surface 24c, instead of the thread ridge 24a. As illustrated in FIG. 7B, this mouthpiece 11 includes a sliding portion 18 having a spiral surface 18a, instead of the thread ridge 14.

With the flavor inhaler 10 employing the flow passage pipe 22 illustrated in FIG. 7A and the mouthpiece 11 illustrated in FIG. 7B, circumferentially turning the mouthpiece 11 slides the spiral surface 18a of the sliding portion 18 along the spiral surface 24c of the spiral protrusion portion 24b of the screw portion 24, thus engaging the sliding portion 18 with the spiral protrusion portion 24b. Thus, the flow passage pipe 22 and the lid member 23 integrated with the screw portion 24 move in the direction of approaching the mouthpiece.

Figure 8:
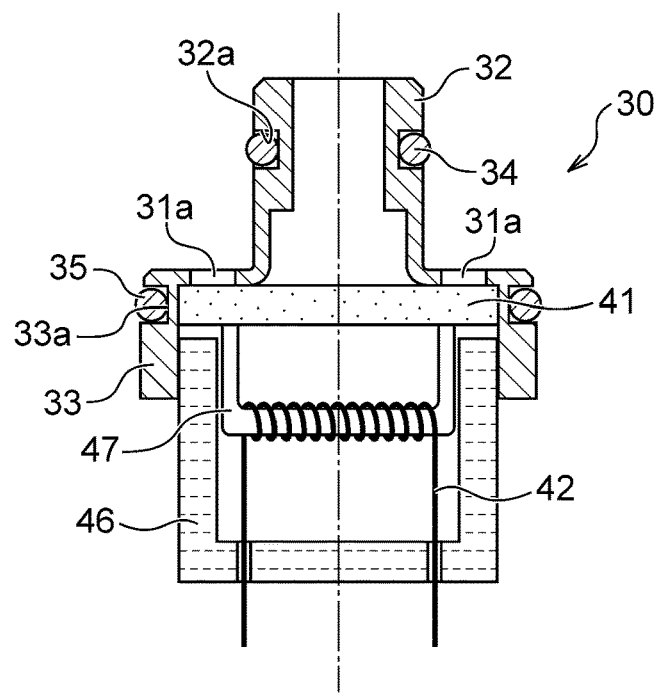
FIG. 8 is a cross-sectional view illustrating another configuration of an atomizing unit provided with the flavor inhaler.

FIG. 8 is a cross-sectional view illustrating another configuration of the atomizing unit 40 provided with the flavor inhaler 10. As illustrated in FIG. 8, the heating wire 42 is spirally formed in a horizontal direction. In other words, the heating wire 42 is spirally formed around an axis approximately perpendicular to the axis in the longitudinal direction of the housing 21 illustrated from FIG. 1 to FIG. 4. The atomizing unit 40 includes a tubular second liquid holding member 47 to hold the liquid supplied from the communication holes 31a. The second liquid holding member 47 is made of glass fiber or similar material. The heating wire 42 is wound around the second liquid holding member 47 to be spirally formed.

With this flavor inhaler 10, the first liquid holding member 41 is formed into a flat plate shape and is located in the atomizing space so as to cover the communication holes 31a on the partition member 30. The end of the second liquid holding member 47 is located to be in contact with the first liquid holding member 41. In view of this, the liquid held in the first liquid holding member 41 moves to the second liquid holding member 47 by capillarity. Supplying the heating wire 42 with the electric power while the second liquid holding member 47 holds the liquid heats the liquid by the heating wire 42 and generates the aerosol.

Figure 9:
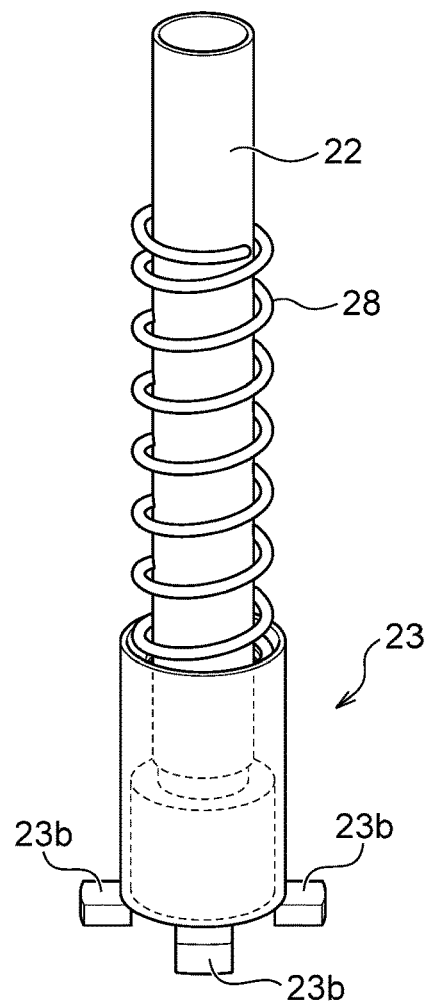
FIG. 9 is a cross-sectional view illustrating another configuration of a lid member provided with the flavor inhaler.

FIG. 9 is a cross-sectional view illustrating another configuration of the lid member 23 provided with the flavor inhaler 10. As illustrated in FIG. 9, the lid member 23 includes a plurality of plate-shaped lid portions 23b projecting in the radial direction. Specifically, the lid member 23 includes the lid portions 23b by the number equivalent to the number of communication holes 31a on the partition member 30. The lid portions 23b partially abut on the plate-shaped portion 31 along the peripheral area of the plate-shaped portion 31 of the partition member 30 to close the communication holes 31a.

Figure 10:
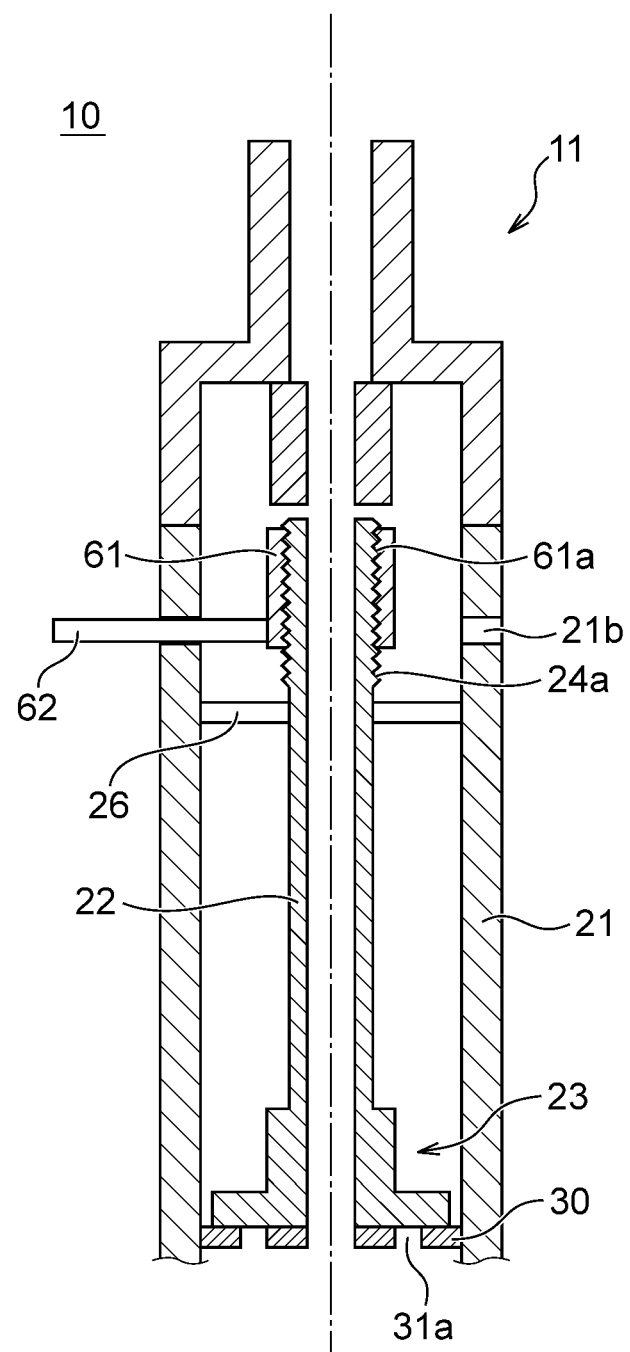
FIG. 10 is a drawing illustrating another example of a motion conversion mechanism provided with the flavor inhaler.
Figure 11:
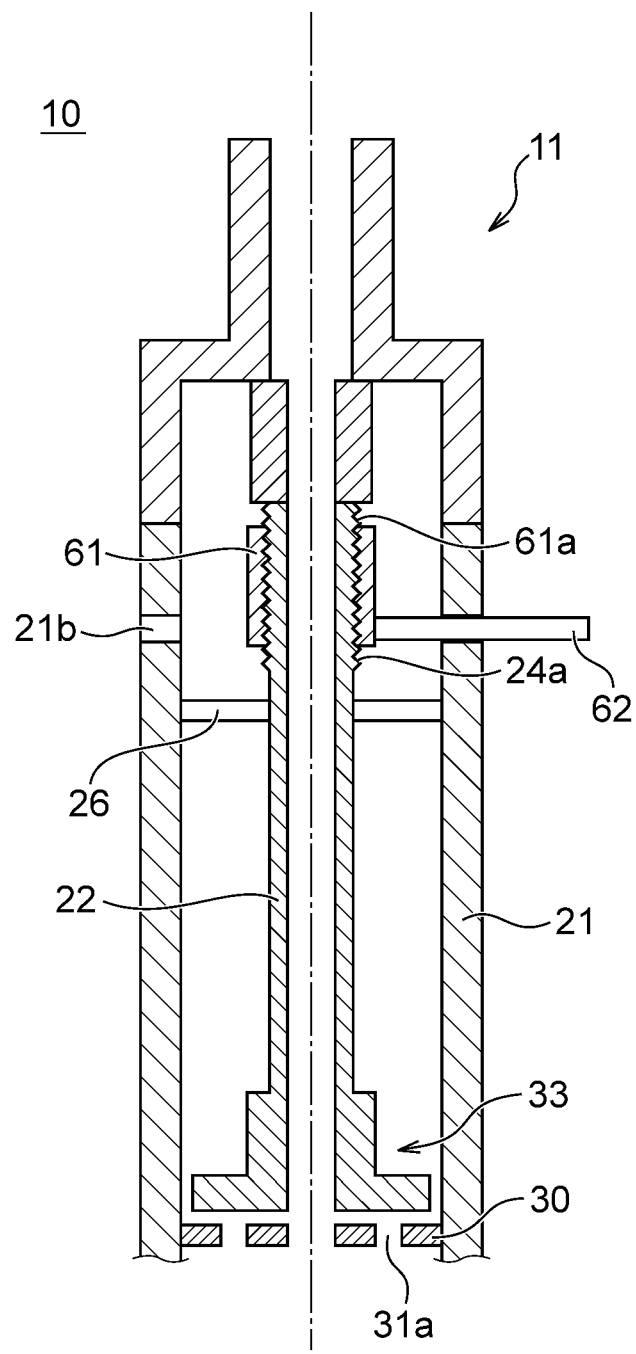
FIG. 11 is a drawing illustrating another example of the motion conversion mechanism provided with the flavor inhaler.

FIG. 10 and FIG. 11 are drawings illustrating other examples of the motion conversion mechanism provided with the flavor inhaler 10. FIG. 10 illustrates a state where the reservoir space and the atomizing space are partitioned, and FIG. 11 illustrates a state where the reservoir space communicates with the atomizing space. FIG. 10 and FIG. 11 omit some components of the flavor inhaler 10. As illustrated in FIG. 10 and FIG. 11, the housing 21 of the flavor inhaler 10 has a cutout 21b, which is formed across the outer peripheral surface by less than 360°. The flavor inhaler 10 includes a turning member 61 threadably engaging with the thread ridge 24a, which is formed on the outer peripheral surface of the flow passage pipe 22. The turning member 61 has a thread ridge 61a, which corresponds to the thread ridge 24a, on the inner peripheral surface. To the turning member 61, a lever 62 partially projecting to the outside of the housing 21 from the cutout 21b is connected.

When the user uses the flavor inhaler 10, the user operates the lever 62 to circumferentially turn the turning member 61. This moves the flow passage pipe 22 and the lid member 23 in the direction of approaching the turning member 61. That is, the thread ridge 61a on the turning member 61 and the thread ridge 24a on the flow passage pipe 22 constitute the motion conversion mechanism that converts the circumferential turning motion of the turning member 61 around the axis parallel to the moving direction of the lid member 23 into an axial linear motion of the lid member 23.

As illustrated in FIG. 11, when the turning member 61 circumferentially turns through the operation of the lever 62, the flow passage pipe 22 and the lid member 23 move in the direction of approaching the turning member 61 and the lid member 23 opens the communication holes 31a on the partition member 30. Accordingly, the reservoir space communicates with the atomizing space. With the flavor inhaler 10 illustrated in FIG. 10 and FIG. 11, the lid member 23 can be opened and closed with the mouthpiece 11 mounted to the housing 21.

Figure 12:
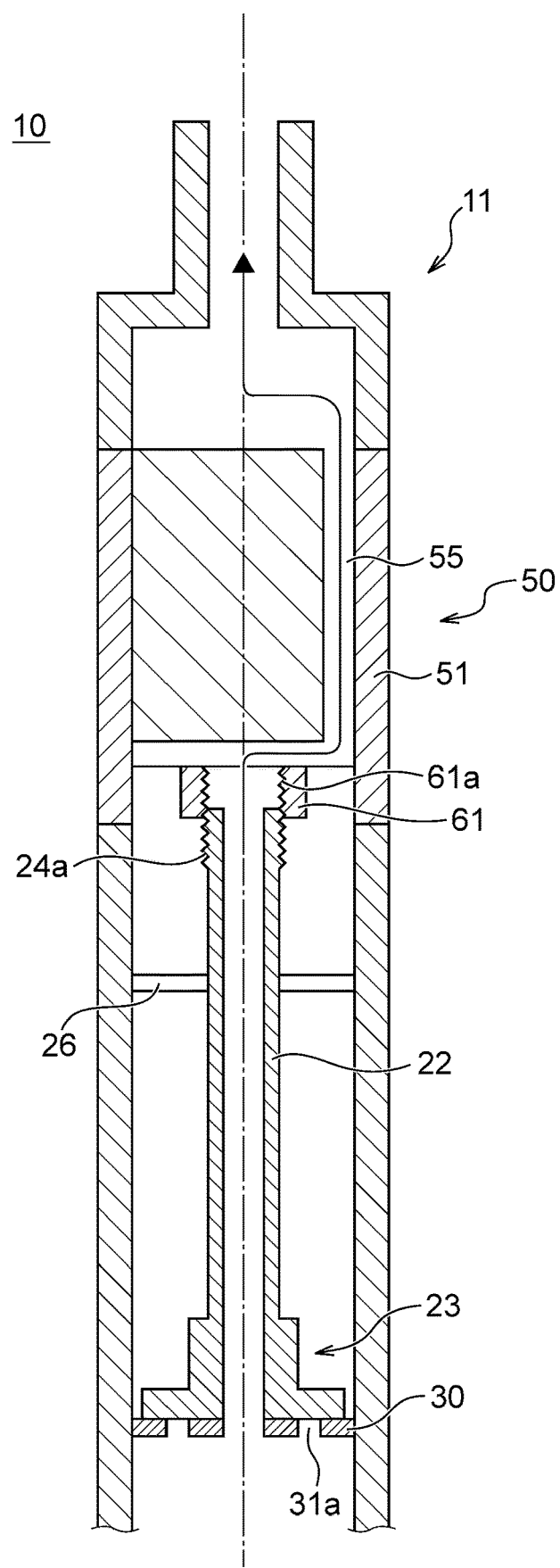
FIG. 12 is a drawing illustrating another example of the motion conversion mechanism provided with the flavor inhaler.

FIG. 12 is a drawing illustrating another example of the motion conversion mechanism provided with the flavor inhaler 10. FIG. 12 omits some components of the flavor inhaler 10. As illustrated in FIG. 12, in this flavor inhaler 10, the battery unit 50 is located between the mouthpiece 11 and the housing 21. FIG. 12 simplifies the illustration of the internal configuration of the battery unit 50. The battery unit 50 includes the turning member 61 threadably engaged with the thread ridge 24a, which is formed on the outer peripheral surface of the flow passage pipe 22. The turning member 61 internally forms a part of the flow passage through which the aerosol supplied from the flow passage pipe 22 passes. The battery unit 50 includes an aerosol flow passage 55 through which the aerosol supplied from the turning member 61 passes.

When the user uses the flavor inhaler 10, the user circumferentially turns the battery housing 51 of the battery unit 50. This moves the flow passage pipe 22 and the lid member 23 in the direction of approaching the turning member 61. That is, the thread ridge 61a on the turning member 61 and the thread ridge 24a on the flow passage pipe 22 constitute the motion conversion mechanism that converts the circumferential turning motion of the turning member 61 around the axis parallel to the moving direction of the lid member 23 into an axial linear motion of the lid member 23.

When the turning member 61 circumferentially turns through the turning of the battery housing 51, the flow passage pipe 22 and the lid member 23 move in the direction of approaching the turning member 61 and the lid member 23 opens the communication holes 31a on the partition member 30. Accordingly, the reservoir space communicates with the atomizing space. With the flavor inhaler 10 illustrated in FIG. 12, the lid member 23 can be opened and closed with the mouthpiece 11 mounted to the housing 21.

While the embodiment of the present invention has been described above, the present invention is not limited to the above-described embodiment. Various modifications are possible within the scope of the technical idea described in the claims, the description, and the drawings. Even when any shape and any material not directly described in the description and the drawings are used, as long as the actions and effects of the present invention are achieved, the configurations are within the technical idea of the present invention.

REFERENCE SIGNS LIST 10 flavor inhaler
11 mouthpiece
11a flow pipe
11b tubular body
13 stepped portion
14 thread ridge
18 sliding portion
18a spiral surface
20 atomizer unit
21 housing
21a opening
22 flow passage pipe
23 lid member
23a lid portion
23b lid portion
24 screw portion
24a thread ridge
24b spiral protrusion portion
24c spiral surface
25 reinforcing member
26 reduction member
27 rib
30 partition member
31 plate-shaped portion
31a communication hole
32 tubular portion
40 atomizing unit
41 first liquid holding member
42 heating wire
47 second liquid holding member
50 battery unit 51 battery housing
61 turning member
61a thread ridge

The invention claimed is:

1. A flavor inhaler cartridge comprising:
a housing that includes a reservoir space to house a liquid and an atomizing space to atomize the liquid;
a movable lid member with which the reservoir space and the atomizing space are openably/closably partitioned;
an aerosol flow passage that supplies an aerosol generated by the atomization of the liquid from the atomizing space to outside of the housing;
a turning member that is circumferentially turnable around an axis parallel to a moving direction of the lid member;
a motion conversion mechanism that converts the circumferential turning motion of the turning member into an axial linear motion of the lid member; and
a moving member that axially moves together with the lid member
wherein the lid member is directly or indirectly fixed to the motion conversion mechanism,
wherein the motion conversion mechanism is configured such that circumferentially turning the turning member moves the lid member in a direction of approaching the turning member and communicates between the reservoir space and the atomizing space,
wherein the lid member is indirectly fixed to the motion conversion mechanism via the moving member,
wherein the motion conversion mechanism is configured such that the circumferential turning motion of the turning member is converted into the axial linear motions of the lid member and the moving member, and
wherein the moving member is a flow passage pipe constituting at least a part of the aerosol flow passage.

2. The flavor inhaler cartridge according to claim 1, wherein the atomizing space internally includes an atomizing element to atomize the liquid.

3. The flavor inhaler cartridge according to claim 1, further comprising a moving member that axially moves together with the lid member,
wherein the lid member is indirectly fixed to the motion conversion mechanism via the moving member, and
wherein the motion conversion mechanism is configured such that the circumferential turning motion of the turning member is converted into axial linear motions of the lid member and the moving member.

4. The flavor inhaler cartridge according to claim 3, wherein the motion conversion mechanism includes:
an engaged portion disposed on an outer peripheral surface or an inner peripheral surface of the moving member; and
an engaging portion engaged with the engaged portion, and
wherein any one of the engaging portion and the engaged portion has a spiral protrusion with a spiral surface, the other of the engaging portion and the engaged portion having a sliding portion sliding on the spiral surface.

5. The flavor inhaler cartridge according to claim 4, wherein the spiral protrusion and the sliding portion are thread ridges.

6. The flavor inhaler cartridge according to claim 1, further comprising a reduction member that reduces a leakage of the liquid in the reservoir space from an opening of the housing to the outside of the housing,
wherein the opening constitutes a supply port to supply the liquid to the reservoir space.

7. The flavor inhaler cartridge according to claim 6, wherein the reduction member is at least partially made of a flexible material.

8. The flavor inhaler cartridge according to claim 1, further comprising a partition member that has a communication hole, the communication hole communicating between the reservoir space and the atomizing space,
wherein the lid member opens and closes the communication hole such that the reservoir space and the atomizing space are openably/closably partitioned.

9. The flavor inhaler cartridge according to claim 1, wherein the turning member is configured to be circumferentially turnable around a center axis of the flow passage pipe.

10. The flavor inhaler cartridge according to claim 1, further comprising a stopper configured to restrict the movement of the lid member,
wherein when the lid member moves in the direction of approaching the turning member by a predetermined distance, the stopper contacts the lid member.

11. The flavor inhaler cartridge according to claim 10, wherein the stopper is located in the reservoir space.

12. The flavor inhaler cartridge according to claim 1, further comprising a moving member that axially moves together with the lid member,
wherein the lid member is indirectly fixed to the motion conversion mechanism via the moving member,
wherein the motion conversion mechanism is configured such that the circumferential turning motion of the turning member is converted into the axial linear motions of the lid member and the moving member, and
wherein the flavor inhaler cartridge further comprises a stopper configured to restrict the movement of the moving member,
wherein when the moving member moves in the direction of approaching the turning member by a predetermined distance, the stopper directly or indirectly contacts the moving member.

13. The flavor inhaler cartridge according to claim 1, further comprising a biasing member configured to bias the lid member to the atomizing space side.

14. The flavor inhaler cartridge according to claim 13, further comprising:
a flow passage pipe that constitutes at least a part of the aerosol flow passage; and
a reinforcing member that reinforces the flow passage pipe,
wherein the biasing member directly or indirectly abuts on the reinforcing member.

15. The flavor inhaler cartridge according to claim 1, wherein the turning member is a mouthpiece, the mouthpiece constituting at least a part of the aerosol flow passage, the mouthpiece being disposed downstream with respect to the reservoir space in the aerosol flow passage.

16. The flavor inhaler cartridge according to claim 15, wherein the mouthpiece includes:
a flow pipe through which the aerosol flows; and
a restricting member configured to contact the housing to restrict an axial movement of the mouthpiece toward the lid member.

17. The flavor inhaler cartridge according to claim 16, wherein the flow pipe is held to the restricting member to be circumferentially turnable, and wherein the motion conversion mechanism is configured to convert the circumferential turning motion of the flow pipe into the axial linear motion of the lid member.

18. The flavor inhaler cartridge according to claim 1, wherein the turning member is located downstream with respect to the lid member in the aerosol flow passage.

19. The flavor inhaler cartridge according to claim 1, further comprising a partition member having a communication hole that communicates between the reservoir space and the atomizing space,
wherein the lid member opens and closes the communication hole such that the reservoir space and the atomizing space are openably/closably partitioned,
wherein the partition member includes a plate-shaped portion that has an opening through which the aerosol generated in the atomizing space passes, the opening constituting at least a part of the aerosol flow passage, and
wherein the communication hole is formed in the plate-shaped portion.

20. The flavor inhaler cartridge according to claim 19, wherein the partition member includes a tubular portion, the tubular portion being joined to the plate-shaped portion, the tubular portion internally communicating with the opening in the plate-shaped portion.

21. The flavor inhaler cartridge according to claim 19, wherein the lid member includes a lid portion, the lid portion abutting on the plate-shaped portion along a whole circumference of the plate-shaped portion to close the communication hole.

22. The flavor inhaler cartridge according to claim 19, wherein the lid member includes a lid portion, the lid portion partially abutting on the plate-shaped portion along a peripheral area of the plate-shaped portion to close the communication hole.

23. The flavor inhaler cartridge according to claim 1, wherein the lid member is located in the reservoir space.

24. The flavor inhaler cartridge according to claim 1, further comprising:
an atomizing element located in the atomizing space to atomize the liquid; and
a partition member having the communication hole that communicates between the reservoir space and the atomizing space,
wherein the lid member opens and closes the communication hole such that the reservoir space and the atomizing space are openably/closably partitioned,
wherein the atomizing element includes a heating wire, and
wherein the heating wire is formed into a spiral shape around an axis approximately parallel to an axis of the housing in a longitudinal direction.

25. The flavor inhaler cartridge according to claim 24, further comprising a first liquid holding member that holds the liquid supplied via the communication hole,
wherein the first liquid holding member is located in the atomizing space.

26. The flavor inhaler cartridge according to claim 25, wherein the first liquid holding member is formed into an approximately tubular shape and has an internal space, and
wherein at least a part of the heating wire is located in the internal space in the first liquid holding member.

27. The flavor inhaler cartridge according to claim 26, wherein the heating wire is formed into a spiral shape around a center axis of the approximately tubular first liquid holding member.

28. The flavor inhaler cartridge according to claim 26, wherein the heating wire of the atomizing element contacts an inner wall of the first liquid holding member.

29. The flavor inhaler cartridge according to claim 25, wherein the first liquid holding member is located in the atomizing space so as to cover the communication hole.

30. The flavor inhaler cartridge according to claim 1, further comprising:
an atomizing element located in the atomizing space to atomize the liquid; and
a partition member having a communication hole that communicates between the reservoir space and the atomizing space,
wherein the lid member opens and closes the communication hole such that the reservoir space and the atomizing space are openably/closably partitioned,
wherein the atomizing element includes a heating wire, and
wherein the heating wire is formed into a spiral shape around an axis approximately perpendicular to an axis of the housing in a longitudinal direction.

31. The flavor inhaler cartridge according to claim 30, further comprising a flat-plate-shaped first liquid holding member that holds the liquid supplied via the communication hole,
wherein the first liquid holding member is located in the atomizing space.

32. The flavor inhaler cartridge according to claim 31, wherein the first liquid holding member is located in the atomizing space so as to cover the communication hole.

33. The flavor inhaler cartridge according to claim 30, further comprising a second liquid holding member that holds the liquid supplied via the communication hole,
wherein the heating wire is wound around the second liquid holding member.

34. The flavor inhaler cartridge according to claim 33, further comprising a flat-plate-shaped first liquid holding member that holds the liquid supplied via the communication hole,
wherein the first liquid holding member is located in the atomizing space, and
wherein the second liquid holding member contacts the first liquid holding member.

35. A flavor inhaler comprising the flavor inhaler cartridge according to claim 1.

36. The flavor inhaler according to claim 35, further comprising:
an atomizing element located in the atomizing space to atomize the liquid; and
an electric power supply unit that supplies the atomizing element with electric power.

37. The flavor inhaler according to claim 36, wherein the electric power supply unit includes the turning member.

* * * * *